United States Patent [19]
Hart

[11] Patent Number: 5,957,133
[45] Date of Patent: *Sep. 28, 1999

[54] ORAL APPLIANCE WITH NEGATIVE AIR SUPPLY FOR REDUCING SLEEP APNEA AND SNORING

[76] Inventor: William T. Hart, 981 Cabernet Ct., Murphys, Calif. 95247

[*] Notice: This patent issued on a continued prosecution application filed under 37 CFR 1.53(d), and is subject to the twenty year patent term provisions of 35 U.S.C. 154(a)(2).

[21] Appl. No.: 08/896,999
[22] Filed: Jul. 21, 1997
[51] Int. Cl.⁶ .............................. A62B 9/06; A62B 7/00; A61M 16/00
[52] U.S. Cl. .............................. 128/207.14; 128/205.19; 128/200.26; 128/207.15
[58] Field of Search ...................... 128/200.26, 201.26, 128/204.11, 204.18, 205.24, 206.29, 207.14, 207.15, 848, 861, 862, 205.19; 137/597

[56] References Cited

U.S. PATENT DOCUMENTS

| | | |
|---|---|---|
| 900,343 | 10/1908 | Barnes . |
| 1,266,856 | 5/1918 | Ramsay .............................. 128/207.14 |
| 2,459,273 | 1/1949 | Freedland . |
| 2,669,988 | 2/1954 | Carpenter . |
| 3,126,002 | 3/1964 | Owens . |
| 3,730,179 | 5/1973 | Williams . |
| 3,905,362 | 9/1975 | Eyrick et al. ....................... 128/205.19 |
| 4,112,936 | 9/1978 | Blachly .............................. 128/207.14 |
| 4,169,473 | 10/1979 | Samelson . |
| 4,170,230 | 10/1979 | Nelson . |
| 4,198,967 | 4/1980 | Dror . |
| 4,260,378 | 4/1981 | O'Neil . |
| 4,270,531 | 6/1981 | Blachly et al. . |
| 4,304,227 | 12/1981 | Samelson . |
| 4,425,911 | 1/1984 | Luomanen et al. . |
| 4,495,945 | 1/1985 | Liegner . |

(List continued on next page.)

FOREIGN PATENT DOCUMENTS

| | | |
|---|---|---|
| 0402951 | 12/1990 | European Pat. Off. . |
| 35 43 931 | 6/1987 | Germany . |
| 35 43 931 A 1 | 6/1987 | Germany . |
| 44 45 652 | 6/1996 | Germany . |
| 44 45 652 A 1 | 6/1996 | Germany . |
| PCT/SE89/ 00500 | 4/1990 | WIPO . |
| WO 90 03199 | 4/1990 | WIPO . |
| PCT/SE90/ 00464 | 1/1991 | WIPO . |
| WO 91 00075 | 1/1991 | WIPO . |

OTHER PUBLICATIONS

W. Schmidt–Nowara, A. Lowe, L. Weigand, R. Cartwright, F. Perez–Guerra and S. Menn—"Oral Appliances for the Treatment of Snoring and Obstructive Sleep Apnea: A Review"—An American Sleep Disorders Association Review—*Sleep 18(6):501–510*—1995 American Sleep Disorders Association and Sleep Research Society, pp. 501–509.

(List continued on next page.)

*Primary Examiner*—Kimberly L. Asher
*Attorney, Agent, or Firm*—Anderson & Adamson, LLP; C. Douglas Defreytas

[57] ABSTRACT

An appliance is provided for installation within the mouth of an individual to prevent obstruction of the natural airway of the individual and to enhance natural ventilation during sleep. The appliance is hollow and constructed of material which is custom-molded to the user. An external negative air supply is provided which connects to a tube extending from the appliance and draws air from the hollow appliance creating a partial vacuum in the user's retroglossal area urging the user's tongue and soft palate away from the user's posterior pharyngeal wall and thereby opening an airway to the user's nasal cavity. A sensor provides control information to the negative air supply by sensing relative pressure in the user's oral cavity. The natural breathing cycle is thus facilitated but not controlled by the appliance.

9 Claims, 2 Drawing Sheets

U.S. PATENT DOCUMENTS

| | | |
|---|---|---|
| 4,513,741 | 4/1985 | Demi . |
| 4,676,240 | 6/1987 | Gardy . |
| 4,856,991 | 8/1989 | Breads et al. . |
| 4,936,298 | 6/1990 | Nishina et al. . |
| 4,938,212 | 7/1990 | Snook et al. . |
| 5,117,816 | 6/1992 | Shapiro et al. . |
| 5,146,913 | 9/1992 | Khorsandian et al. . |
| 5,181,505 | 1/1993 | Lew et al. . |
| 5,195,513 | 3/1993 | Sinko et al. . |
| 5,203,324 | 4/1993 | Kinkade . |
| 5,443,060 | 8/1995 | Visveshwara et al. . |
| 5,465,734 | 11/1995 | Alvarez et al. . |
| 5,507,282 | 4/1996 | Younes . |
| 5,522,382 | 6/1996 | Sullivan . |
| 5,626,128 | 5/1997 | Bradley et al. . |

OTHER PUBLICATIONS

Standards of Practice Committee of the American Sleep Disorders Association and Sleep Research Society—"Practice Parameters for the Treatment of Snoring and Obstructive Sleep Apnea with Oral Appliances"—*Sleep 18(6):511–513*—1995 American Sleep Disorders Association and Sleep Research Society, pp. 511–513.

Promotional Pamphlet "The Klearway Oral Appliance", Great Lakes Orthodontics, Ltd., 1995, 12 pages.

Article "Snoring, A Reason to be Concerned", Great Lakes Orthodontics, Ltd.—2 pages.

Promotional Sheet "The Snore Appliance", Dyna Flex., Ltd., St. Louis, MO—1 page.

Promotional Pamphlet "Nocturnal Airway Patency Appliance", Great Lakes Orthodontics, Ltd., 12 pages.

Promotional Pamphlet "The Elastomeric Sleep Appliance", Great Lakes Orthodontics, Ltd., 4 pages.

Article "Snoring The Universal Language" and "The Virginia Partial", Johns Dental Laboratories, Oral Support, Winter 95/96, 2 pages.

D. L. GRIM Newsletter, Medical Resource Center, Olympia, WA, 3 pages.

Promotional Sheet "Silencer", Johns Dental Laboratories, Terre Haute, IN, 1 page.

Patrick Leger, MD and Susan Sorter Leger, RRT, "The Art of Interface, Tools for Administering Noninvasive Ventilation", InterVENTions a ventilatory care newsletter published by Respironics, Spring 1997, vol. 2, pp. 4–11.

John R. Bach, MD, FCCP and Augusta S. Alba, MD, "Sleep and Nocturnal Mouthpiece IPPV Efficiency in Postpoliomyelitis Ventilator Users", *Chest*, 106, 6, Dec., 1994, pp. 1705–1710.

John R. Bach, MD ; Augusta S. Alba, MD; George Bohatiuk, MD; Lou Saporito, RRT; and Mattew Lee, MD., "Mouth Intermittent Positive Pressure Ventilation in the Management of Postpolio Respiratory Insufficiency", *Chest*, 91, Jun. 6, 1987, pp. 859–864.

John R. Bach, MD, "Mechanical Exsufflation, Noninvasive Ventilaiton, and New Strategies for Pulmonary Rehabilitation and Sleep Disordered Breathing", *Pulmonary Rehavilitation*, Bull. N.Y. Acad. Med., vol. 68, No., 2, Mar.–Apr. 1992, pp. 321–340.

John R. Bach, MD, Letter to the Editor "Mask Ventilation Doesn't Have to Be through the Nose", *Chest*, 101, Apr. 4, 1992, pp. 1182–1183.

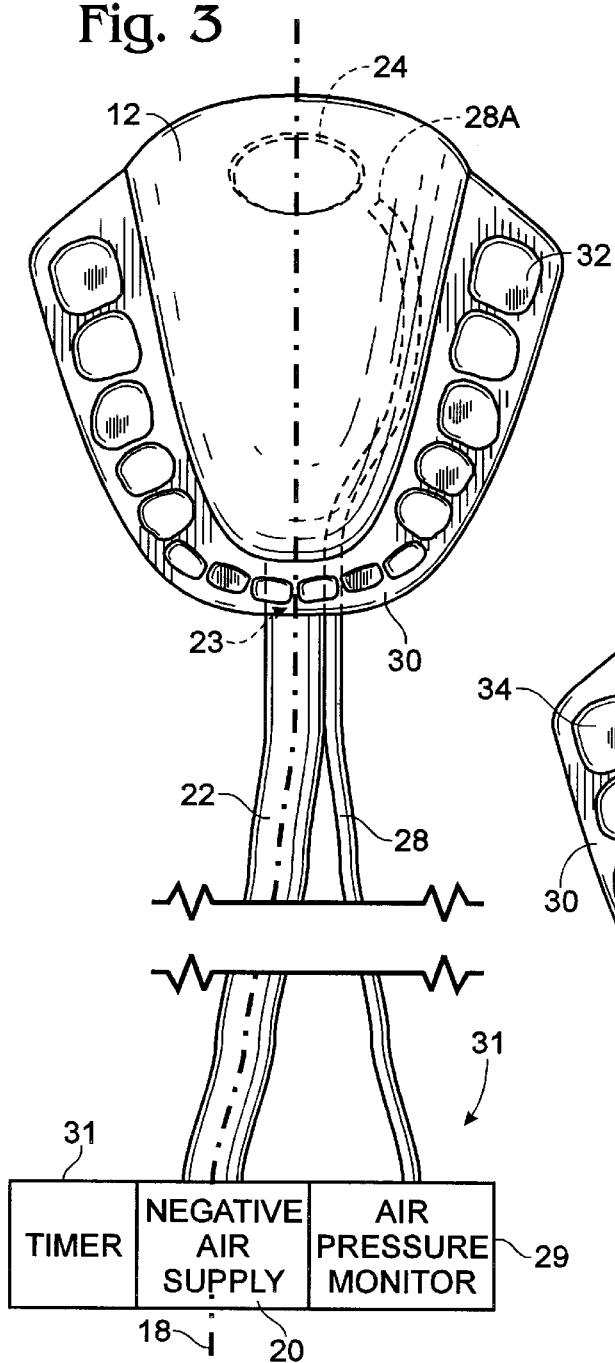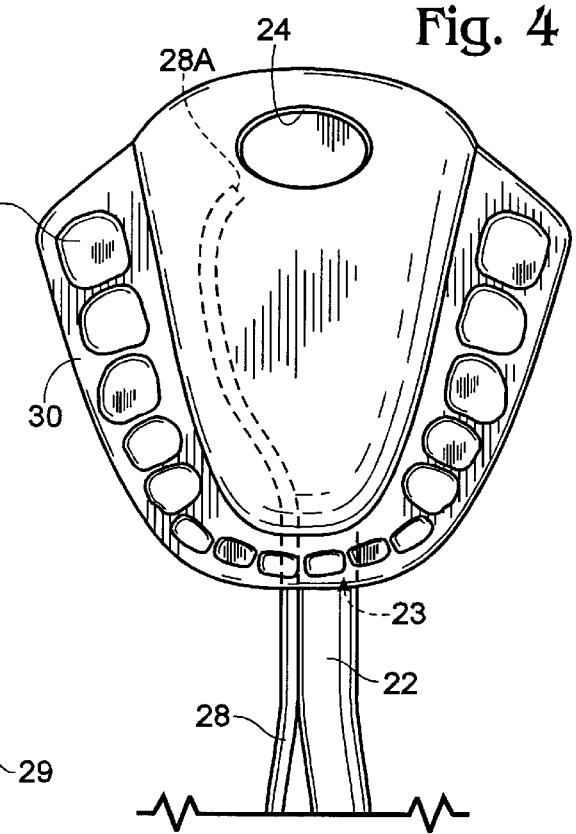

ORAL APPLIANCE WITH NEGATIVE AIR SUPPLY FOR REDUCING SLEEP APNEA AND SNORING

CROSS-REFERENCE TO RELATED APPLICATIONS

This is related to my copending U.S. patent application Ser. No. 08/677,491, filed on Jul. 9, 1996.

BACKGROUND OF THE INVENTION

1. Field of the Invention

This invention relates to appliances for preventing airway occlusion during sleep in individuals who suffer from sleep apnea or snoring, or both. More particularly it relates to an appliance that is inserted into a user's oral cavity and connected to an external negative air pressure source. In normal operation the vacuum created by the negative air pressure urges the user's tongue and soft palate anteriorly and away from the user's posterior pharyngeal wall.

Airway occlusion during sleep produces increased airway resistance to airflow and may cause cessation of breathing (apnea) and lead to undesirable physiologic changes of hypoxemia and hypercapnia. Persons suffering from sleep apnea are at risk for systemic and pulmonary hypertension, arrhythmias leading to sudden cardiac death, and accidents due to hypersomnolence.

Airway occlusion may be caused by decline in upper airway dilator muscle tone, especially the genioglossus muscle. Redundant pharyngeal tissue and edema may be contributing factors. Sleeping on the back may exacerbate airway occlusion due to the added effect of gravity on the tongue and soft palate. Sleep apnea is most pronounced during the inspiratory phase of breathing (inhalation). In patients suffering from sleep apnea or snoring, or both, the retroglossal area is usually the most obstructed part of the airway.

2. Description of Related Art

Various devices have been developed to facilitate breathing for those suffering from airway occlusion. One such device, as disclosed in U.S. Pat. No. 4,676,240, issued to Gardy on Jun. 30, 1987, provides a mechanism which holds the tongue forward in a vacuum chamber. Another device is disclosed in U.S. Pat. No. 4,170,230, issued to Nelson on Oct. 9, 1979, which allows the user to breathe through his or her mouth without drying out the mouth. Another device, as disclosed in U.S. Pat. No. 4,198,967, issued to Dror on Apr. 22, 1980, teaches a method of holding the tongue in an unconscious or semi-conscious individual as an adjunct to resuscitation of the individual.

U.S. Pat. No. 3,370,179, issued to Williams on May 1, 1973, discloses a resuscitating apparatus which includes a tube extended down the throat of a victim in combination with a draining apparatus.

None of these inventions provides for urging the tongue and soft palate anteriorly and away from the posterior pharyngeal wall by applying a partial vacuum through a device inserted into a user's oral cavity.

SUMMARY OF THE INVENTION

The present invention overcomes limitations of the existing art. Specifically, it prevents airway occlusion during sleep, minimizing sleep apnea and snoring, by maintaining adequate opening in a user's retroglossal area by providing negative air pressure directly into the oral cavity to urge the tongue and soft palate away from the posterior laryngeal wall, opening the airway through the nasal passage to facilitate natural breathing. It further provides a simple, comfortable appliance, operable by a patient without direct medical assistance, to reduce the deleterious effects of sleep apnea and snoring.

In the preferred embodiment of the present invention, a hollow body is molded to the user's oral cavity and includes an integral, generally C-shaped lip-like member conforming to the user's bite impression. The appliance is thus natural and comfortable when inserted in the user's oral cavity. Furthermore, the molded design naturally secures the appliance in the desired position during use with no effort by the user, which is a necessary feature inasmuch as the appliance is intended to be worn while the user is asleep. One embodiment of the present invention further includes a sensor tube extending through the user's teeth and lips, for connection to an air pressure monitor which controls the external negative air supply.

At the rear of the body of the present invention the body forms an opening through which a partial vacuum is drawn in the user's oral cavity.

The typical and undesirable characteristic of a patient suffering from sleep apnea or snoring is the tendency of the tissues in the retroglossal area, typically the posterior portion of the tongue and the soft palate, to rest against the posterior laryngeal wall, blocking the airway from the lungs to the nasal passage, interfering with normal breathing. The present invention effectively prevents such blockage by pulling the tongue and soft palate away from the posterior laryngeal wall by creation of a partial vacuum in the oral cavity, maintaining an open airway from the user's lungs through the nasal passage to outside atmosphere.

In one embodiment, a second tube extends from the hollow body of the appliance, through the user's teeth and lips, to the external negative air supply, providing feedback to regulate the application of negative air pressure. These and other advantages and features of the present invention will be apparent from the preferred embodiment described in the following detailed description and in the accompanying drawings.

BRIEF DESCRIPTION OF THE DRAWINGS

FIG. 3 is a plan view of the appliance of FIG. 1 showing connection to an air pressure source.

FIG. 4 is a bottom view of the appliance of FIG. 1 showing the opening which is situated in a user's oral cavity.

DETAILED DESCRIPTION OF THE PREFERRED EMBODIMENTS

Figure 1:
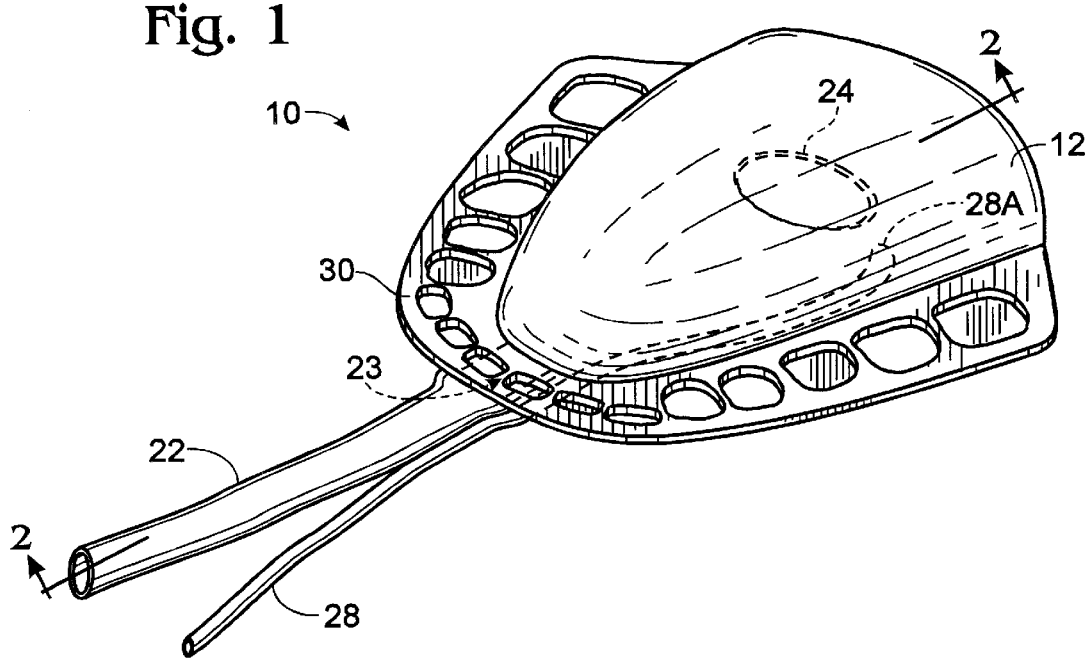
FIG. 1 is a perspective view of an appliance made according to the invention.
Figure 2:
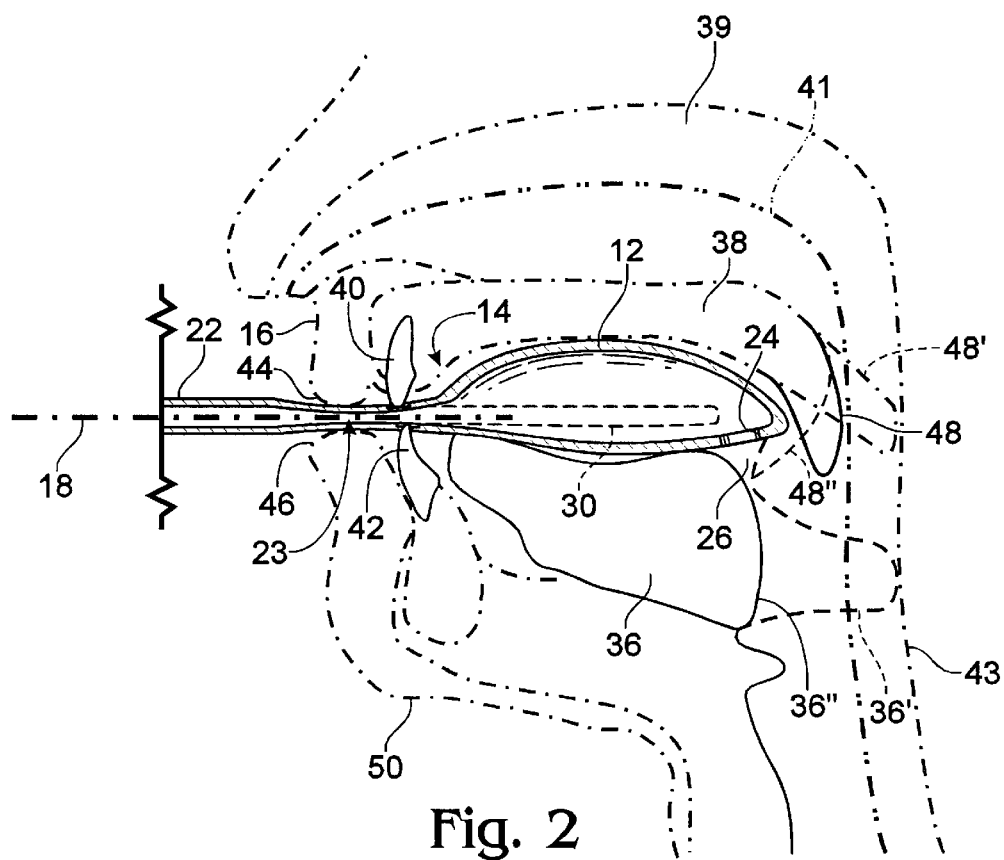
FIG. 2 is a cross-sectional view taken generally along the line 2—2 of FIG. 1 illustrating the appliance of FIG. 1 inserted an a user's oral cavity.

Referring to the drawings, an oral appliance constructed in accordance with the present invention is shown generally at 10 in FIG. 1. FIG. 2 depicts a cross-sectional view of the appliance taken along line 2—2 in FIG. 1, illustrating a hollow body 12 of the appliance installed in the oral cavity 14 of a user 16.

In FIG. 3 a top view of the appliance is shown illustrating an air pathway 18 from an external negative air supply 20, through a tube 22, into a first opening 23 in the body, through hollow body 12, to a second opening 24, which, in the operative position, opens in the user's retroglossal area 26 as seen in FIG. 2. Body 12 thus forms what is also referred to as an enlarged chamber extending between the first and second openings. As can be seen, one end of tube 22 is attached to body 12 to provide fluid communication through opening 23 between the enlarged chamber in body 12 and the exterior of the user's oral cavity. Accordingly, tube 22 and body 12 define what is also referred to as an air supply pathway.

Referring again to FIG. 3, a second tube 28 is shown communicating from a point adjacent to opening 24, following generally alongside tube 22, and connected to the external negative air supply 20. Air supply 20 is a conventional negative air supply, such as one having the proprietary name Care-E-Vac-ac sold by Aeros (Gurnee, Ill.) Instruments. Tube 28 is connected to a conventional air pressure monitor 29 such as Model No. 302220 also sold by Respironics, Inc. Tube 28 and monitor 29 form what is generally referred to as a sensor 31.

A lip 30 as seen in FIGS. 1, 3, and 4 extends out from the anterior outer edges of body 12. Lip 30 is integrally attached to body 12 and includes indentations, such as shown at 32, 34. These indentations are preferably formed as dental impressions using conventional techniques. When installed in a user's oral cavity, as shown in FIG. 2, the appliance lodges vertically between the user's tongue 36 and the user's hard palate 38. Passing between user's teeth, such as upper tooth 40 and lower tooth 42, and between the user's lips including upper lip 44 and lower lip 46, tube 22 is seen to communicate outside the user's oral cavity 14 Appliance 10 is naturally held in proper operative position by the shape of body 12 conforming nestingly to the user's oral cavity 14, bounded by tongue 36, and hard palate 38. Accordingly, a user's tooth, corresponding to, and naturally nesting in an associated indentation 32, assists in holding appliance 10 in the desired position in the user's oral cavity 14. Another user's tooth, corresponding to and naturally nesting in indentation 34, further assists in securing the appliance. Similarly, all of the user's teeth will have corresponding indentations in lip 30, such that appliance 10 is securely held immobile with reference to the user's oral cavity 14 when installed by user 16.

In the embodiment particularly shown in FIG. 3, appliance 10 is installed in a user's oral cavity 14 and connected to external negative air supply 20 with tube 22. During normal use, negative air supply 20 is turned on when the user goes to sleep, and remains on constantly. An optional sensor 31 uses a second tube 28, which terminates at end 28A near opening 24.

In operation, air is drawn from hollow body 12, via tube 22 by air supply 20, when triggered by monitor 29 or timer 31. Monitor 29 is designed to sense the decreased pressure in tube 28 during inhalation if the user's soft palate 48 and tongue 36 fall posteriorly against posterior laryngeal wall 43 closing the airway through the nasal passage 39, as shown by soft palate 48' and tongue 36'. Air is then evacuated through body 12 creating a partial vacuum in oral cavity 14 and urging the soft palate and tongue into the positions shown at 48" and 36", thereby reopening airway 41 extending through the user's nasal passage 39. In one embodiment the air supply is turned off by timer 31 after a given duration and remains off unless decreased air pressure, caused by the user's attempt to inhale, is sensed if the user's soft palate should block airway 41 again.

Air supply 20 preferably generates a selected negative pressure in the range of −5 to −70 cm of H2O pressure. The normal negative inspiratory pressure in the throat and lungs due to muscular contraction of the diaphram and chest wall has been found to be in the range of −5 to −10 cm H2O. Subatmospheric intraluminal pressure generated during inspiration leads to occlusion of the collapsable airway by creating apressure gradient. In obstruction the collapsable upper airway is not able to remain patent at intraluminal subatomic pressures.

When a negative pressure is applied to appliance 10 from air supply 20, a subatmospheric pressure is generated in the oral cavity and pharynx, thereby eliminating the occlusive pressure gradient created by the subatmospheric intraluminal pressure generated during inspiration. Elimination of the pressure gradient opens the upper airway, allowing positive pressure ambient airflow to occur through the nasal passages in a manner similar to normal nasal breathing during sleep. The nasal route of breathing has been observed in normal individuals to be the primary method of breathing during sleep and wakefulness.

The subatmospheric pressure generated in the oral cavity and pharynx also has a stabilizing effect on the soft palate and redundant collapsable tissues, thereby reducing and eliminating snoring. Relief of the obstruction produces improved ventilation, easier breathing, and normalization of the physiological derangements of hypoxemia, hypercapnea, and apnea.

Use of the invention is initially monitored, with different pressures applied by air source supply 20. A pressure, typically in the range of −20 to −50 cm of H2O pressure, is then selected that is most effective for the particular user.

In the preferred embodiment of the present invention, appliance 10 is tailored to an individual user's oral cavity from tooth impressions as conventionally known. It will be understood by those familiar with the art that "tooth impressions" in the present context includes impressions of a user's bony oral cavity structure where the user lacked full dentition, or lacked teeth altogether.

To manufacture an appliance in accordance with the present invention, a moldable, hollow body 12 the approximate size of a user's oral cavity is formed. Then, a moldable, resilient, horseshoe-shaped lip 30 is formed which protrudes concentrically from the body 12. The body 12 with lip 30 is then inserted into the user's oral cavity, while the material is still moldable, the user clenches his or her teeth on lip 30 and the appliance 10 is molded in conformance with the user's oral cavity structure. First and second openings 23 and 24 are then formed on the molded appliance. A tube 22 is then attached to first opening 23. If desired, a second tube 28 is then attached through first opening 23 so that it extends through hollow body 12 to a point adjacent to second opening 24.

During the impression-taking phase of manufacture of the appliance, the user's lower jaw is held slightly forwardly from a relaxed-jaw position. When the finished appliance is installed by the same user, the nestling effect described herein urges the user's lower jaw 50 to a slightly forward position from a relaxed-jaw state. This feature further enhances the operation of the appliance by holding the user's tongue 36 forward and away from the user's pharyngeal wall 43, assisting in avoiding constriction caused by the juxtaposition of the tongue 36 and the soft palate 48.

It will thus be appreciated that appliance 10 provides improved treatment of occlusive sleep apnea. A defined, unrestricted airway is provided through the user's nasal passage and the retroglossal area. An optional timer deactivates the negative air supply until the need for activation is sensed. The appliance conforms to the user's oral cavity and teeth, making it comfortable to use. Variations in form and detail of the preferred embodiment may be made without departing from the scope of the described invention as literally set forth in the claims and as provided under the doctrine of equivalents. For example, the appliance body could be made smaller, it only being necessary to apply a negative pressure to the user's oral cavity, and other means could be used to anchor the body in the oral cavity.

What is claimed is:

1. An oral appliance for facilitating breathing comprising:
a hollow body defining an air supply pathway and adapted for insertion into a user's oral cavity, the body having a first opening in one end, a second opening in the other end positioned during use in the user's retroglossal area, and an enlarged chamber extending between the first and second openings, the body being adapted to fill the oral cavity between the entire upper surface of the tongue and the palate of the user when inserted; and
an external negative air pressure source coupled to the body first opening for applying negative air pressure through the body to the second opening when the body is placed in a user's oral cavity with the first opening positioned anteriorly, and thereby applying negative air pressure to the retroglossal area.

2. The oral appliance of claim 1 further comprising a lip formed integrally with the body and extending from the body for grasping between the user's teeth.

3. The oral appliance of claim 2 in which the lip extends continually around the one end of the body and is formed from a molded dental impression of the user's oral cavity formed with the user's lower jaw positioned slightly anteriorly from a relaxed-jaw position in relation to the upper jaw.

4. The oral appliance of claim 1 further comprising a sensor for sensing air pressure in the enlarged chamber, the source being responsive to the sensor for applying negative air pressure to the enlarged chamber when a relatively negative air pressure is sensed.

5. The oral appliance of claim 1 in which the body has an upper surface that is formed of a molded impression of the user's palate.

6. The oral appliance of claim 1 wherein the body has a lower surface facing the user's tongue during use that is formed of a molded impression of the user's palate.

7. The oral appliance of claim 2 wherein the enlarged chamber conforms to the shape of the body.

8. An oral appliance for facilitating breathing comprising:
a hollow body adapted for complete insertion into a user's oral cavity, the body defining an air pathway and composed of a molded material spatially conforming to the user's oral cavity and including a first opening positioned anteriorly during use and a second opening positioned posteriorly during use in the user's retroglossal area;
a lip extending from the body sagitally and anteriorly during use for grasping between the user's teeth, the lip formed from upper and lower dental impressions of the user's teeth for holding the user's teeth slightly apart and the user's lower jaw slightly forward from a relaxed-jaw position when placed in the user's oral cavity with the teeth positioned in the dental impressions, the lip molded to form a first opening;
a sensor for sensing air pressure in the body adjacent to the second opening;
a tubular member coupled at one end to the lip for communication with the first opening, the other end extending distally of the lip; and
an air pressure source coupled to the other end of the tubular member and responsive to the sensor, for applying negative air pressure through the body to the second opening when a relatively negative air pressure is sensed.

9. An oral appliance for facilitating breathing comprising:
a hollow body defining an air supply pathway and having an opening positioned posteriorly during use in the user's retroglossal area, the body being adapted to fill the oral cavity between the entire upper surface of the tongue and the palate of the user when inserted;
a lip attached to the body and extending along a length of the body for grasping between the user's teeth and thereby securing the body in the oral cavity with the opening positioned in the retroglossal area; and
an external negative air pressure source coupled to the body for applying negative air pressure through the body to the opening when the body is placed in a user's oral cavity, and thereby applying negative air pressure to the retroglossal area.

\* \* \* \* \*